United States Patent [19]

Klaveness et al.

[11] Patent Number: 5,725,840
[45] Date of Patent: Mar. 10, 1998

[54] STEROIDAL ESTER CONTRAST MEDIA FOR X-RAY AND MAGNETIC RESONANCE IMAGING

[75] Inventors: Jo Klaveness; Frode Rise, both of Oslo, Norway; John Varadarajan, Sunnyvale, Calif.; Arne Jørgen Aasen, Jar, Norway

[73] Assignee: Nycomed Imaging AS, Oslo, Norway

[21] Appl. No.: 669,383

[22] PCT Filed: Jan. 13, 1995

[86] PCT No.: PCT/GB95/00065

§ 371 Date: Oct. 4, 1996

§ 102(e) Date: Oct. 4, 1996

[87] PCT Pub. No.: WO95/19186

PCT Pub. Date: Jul. 20, 1995

[30] Foreign Application Priority Data

Jan. 13, 1994 [NO] Norway ................... 940 115

[51] Int. Cl.$^6$ ............... A61K 49/00; C07F 5/00; C07C 69/96
[52] U.S. Cl. ............ 424/9.36; 424/9.4; 424/9.42; 424/9.45; 424/9.455; 534/15; 534/16; 540/3; 540/120; 558/270; 558/275
[58] Field of Search ............ 534/15, 16; 540/3, 540/120; 558/270, 275; 424/9.36, 9.42, 9.45, 9.455, 9.4

[56] References Cited

U.S. PATENT DOCUMENTS

| | | | |
|---|---|---|---|
| 3,793,350 | 2/1974 | Crabbé | 260/397.45 |
| 4,060,606 | 11/1977 | Daehne et al. | 424/238 |
| 4,567,034 | 1/1986 | Charles et al. | 424/5 |
| 4,874,855 | 10/1989 | Takagaki et al. | 540/3 |
| 4,948,533 | 8/1990 | Braughler et al. | 552/576 |
| 5,322,679 | 6/1994 | Bacon et al. | 424/5 |
| 5,370,861 | 12/1994 | Klaveness et al. | 424/5 |
| 5,384,107 | 1/1995 | Singh et al. | 424/5 |
| 5,416,223 | 5/1995 | Klaveness et al. | 549/65 |
| 5,482,700 | 1/1996 | Deutsch et al. | 424/9.364 |
| 5,622,944 | 4/1997 | Hale et al. | 514/181 |

FOREIGN PATENT DOCUMENTS

| | | |
|---|---|---|
| 0 603 922 | 6/1994 | European Pat. Off. |
| 0 603 923 | 6/1994 | European Pat. Off. |
| 90 07491 | 7/1990 | WIPO |
| 92 17212 | 10/1992 | WIPO |

OTHER PUBLICATIONS

Iida et al., *Journal of Organic Chemistry*, 47, 1982, 2978–2981.

Longino et al., *Investigative Radiology*, vol. 18, pp. 275–278 (1983).

*Primary Examiner*—John Kight
*Assistant Examiner*—Lara C. Kelley
*Attorney, Agent, or Firm*—Bacon & Thomas

[57] ABSTRACT

The present invention relates to metabolically labile esters, and to contrast media for X-ray and magnetic resonance imaging comprising these esters. The esters have formula (I):

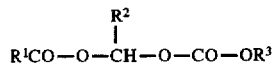

in which $R^3$ is asteroid residue. The esters contain at least one iodine atom and/or heavy metal atom. The compound are metabolizable to products which are soluble in body fluids and are physiologically acceptable.

10 Claims, No Drawings

STEROIDAL ESTER CONTRAST MEDIA FOR X-RAY AND MAGNETIC RESONANCE IMAGING

This application is a 371 of PCT/GB95/00065, filed Jan. 13, 1995 published as WO95/19186 Jul. 20, 1995.

The present invention relates to contrast agents for medical X-ray and/or magnetic resonance imaging, and to their preparation and use.

It has been proposed to improve the detection of lesions in the liver, suprarenal glands and spleen by the use of contrast agents which accumulate in these organs. A number of substances have been suggested but there is no such product on the market at the present time and each of the contrast agents so far proposed has some disadvantages.

Since the reticuloendothelial system of the liver and spleen is well known to trap particles by phagocytosis, contrast agents in particulate form are particularly well adapted for visualisation of these organs.

Emulsions of iodinated oils have been proposed in this context, particularly iodinated ethyl esters of poppy seed oil. (Vermess, M. et al., Radiology, 137 (1980) 217). However, these substances have proved to be unduly toxic.

Another possibility for X-ray diagnosis is to use liposomes containing water soluble iodinated contrast agents. (Havron, A., et al., Radiology, 140 (1981) 507). However, since only a limited amount of iodine can be incorporated in each liposome, it is necessary to administer relatively large amounts of lipids in order to attain adequate contrast enhancement. This tends to cause emboli in the lung capillaries. Furthermore, liposomes have been found to be relatively unstable on storage. (Shulkin, P. M., et al., J. Microencapsul., 1 (1984) 73).

Submicron thorium dioxide particles have been used for liver visualisation and have shown effective enhancement of contrast in clinical testing but their use has been discontinued because of the extremely lengthy retention of the particles in the liver. This, in combination with the inherent radioactivity of thorium, has led to serious adverse side effects, including neoplasm and fibrosis. (Thomas, S. F., Radiology, 78 (1962) 435).

It has also been proposed to use particles comprising the ethyl ester of the water soluble X-ray contrast agent iodipamide (Violante, M. R., et al., Invest. Radiol., 2 (1984) 133). However, ethyl esters are not sufficiently metabolically labile and thus would be expected to be retained in the liver for a considerable period. Both this ester and an iodinated ethyl ester of poppy seed oil gave an increase in lipid vacuoles in the hepatocytes after intravenous administration. (Vermess et al., Radiology, 137 (1980) 217 and Violante, M. R., Invest. Radiol., 2 (1984) 133). Such morphological changes indicate an adverse effect on the hepatocytes.

For magnetic resonance imaging a number of paramagnetic and ferromagnetic/superparamagentic particles are proposed for visualisation of the liver and spleen (Watson, A. D. et al., chapter 14 in Stark, D. D. et al., Magnetic Resonance Imaging, 2nd edition Mosby Year Book 1992 and Fahlvik, A. K., J. Magnetic Resonance Imaging, 3, (1993), 187). However, these particulate products have proved to be unduly toxic.

Another possibility for magnetic resonance imaging of the liver in particular is to use water soluble paramagnetic chelates such as the manganese (2+) chelate of N,N'-bis (pyridoxal-5-phosphate)ethylenediamine-N,N'-diacetic acid (MnDPDP), the gadolinium (3+) chelate GdBOPTA where the chelator BOPTA has a diethylene triamine pentaacetic acid (DTPA) structure in which one of the N-carboxymethyl groups is replaced by a 2-benzyloxy-1-carboxyethyl group, or the gadolinium (3+) chelate GdEOB-DTPA where the chelator EOB-DTPA means ethoxybenzyl-DTPA (de Haén, C. et al., J. Magnetic Resonance Imaging, 3 (1993) 179).

Liposomes containing water soluble paramagnetic chelates have been proposed as contrast media for magnetic resonance imaging of the liver (Unger, E. C., J. Magnetic Resonance Imaging 3 (1993) 195). However, liposomes have, as earlier pointed out, proven to be relatively unstable on storage (Shulkin, P. M. et al., J. Microencapsul 1 (1984) 73).

The proposed liver contrast agents for magnetic resonance imaging all have disadvantages, including being unduly toxic (Øksendal, A. N. et al., J. Magnetic Resonance Imaging 3 (1993) 157).

Steroids have been proposed for a number of contrast media for the liver and suprarenal glands. Different sterols (steroid alcohols) are for example proposed as components in liposome/micelle membranes in contrast media (Squibb in U.S. Pat. No. 4,192,859, Micro-pak in WO 8900812, Vestar in U.S. Pat. No. 4,728,575, Unger in WO 9004943, WO 9109629 and WO 9222247, Terumo in JP 4312535, Micro Vesicular Systems and Micro-pak in U.S. Pat. No. 4,911, 928, Hoffmann La-Roche in EP 388817, University of Massachusetts in U.S. Pat. No. 4,544,545 and Merck in EP 28917). Steroids have also been proposed as components in pharmaceutical suspensions including contrast media (Sterling Drug in GB 867650).

Another possibility consists of using steroids as components in various emulsions which can be utilized as contrast media (Alliance Pharmaceuticals and Fluoromed Pharmaceuticals in EP 231070, Kabi Pharmacia in WO 9218169).

Cholesterol is further proposed as a stabiliser of ultrasound contrast media (Hoechst in U.S. Pat. No. 5,190,982 and U.S. Pat. No. 5,205,287, Nycomed Imaging in WO 9313808, Sterling Winthrop in U.S. Pat. No. 5,196,183 and Schering in DE 3313946 DE 3313947 and DE 3834705).

Sterols are also proposed as carriers of paramagnetic chelates in contrast media for Magnetic Resonance imaging (Green Cross in JP 5186372, Research Corp Technologies in WO 9114178, Nat. Inst. of Health in U.S. Pat. No. 4,923, 985, Du Pont de Nemours in EP 196669, US Dep. of Commerce et al., in WO 9114458 and WO 8911475 and Abbott in EP 279307).

Other diagnostic possibilities for steroids include using fluorinated amino acid steroid derivatives (Applications et Transferts de Technologies Avancees in EP 311473), bile acid-sulphonamide derivatives for diagnosis of intestinal bacteria (Takahashi in JP 3138993) and radioactively labelled cholesterol as a scintigraphic medium for visualisation of the liver and suprarenal glands (Inst. Endokrinologi Khimii in SU 1346137).

Acyloxyalkyl esters of carboxy acids which contain a triiodophenyl group are known contrast media from GB-A-1363847, U.S. Pat. No. 4,018,783, GB-A-2157283, WO 8900988 and WO 9007491. In U.S. Pat. No. 4,018,783 the compounds are primarily proposed for X-ray imaging of the bronchial system, while the most preferred use according to GB-A-2157283 is in a liposome carrier for lymphography.

WO 8900988 and WO 9007491 relate to particulate compounds primarily proposed as X-ray contrast agents for liver and spleen.

However, all of the proposed contrast media for X-ray and magnetic resonance imaging for visualisation of the liver, suprarenal glands and spleen have proven to have disadvantages such as difficulty in formulation, stability problems, unfavourable pharmacology or being unduly toxic.

We have now surprisingly discovered that carbonate esters of formula I which contain a contrast agent acid and which also are formed from asteroid alcohol (sterol) are particularly favourable as X-ray and magnetic resonance imaging contrast media. Such contrast media may be used for different tissue types, organs and organ systems, but the preferred use is visualisation of the liver, suprarenal glands and spleen. The contrast agent acid may be an iodine- or heavy metal atom-containing substance. Carbonate esters are hydrolyrically very stable, but metabolically labile and in the target organ form water soluble substances which are nearly non-toxic. The sterol is the carrier of the contrast agent to the target organ and the choice of sterol is of great significance for the rate of uptake and distribution of the contrast agent in the organism.

According to the present invention we provide metabolically labile esters of the formula (I):

wherein

R$^1$ is a substituted or unsubstituted C$_{1-20}$-aliphatic, C$_{7-20}$-araliphatic or C$_{6-20}$-aryl group or a C$_{1-20}$-heterocyclic group having one or more hetero atoms selected from O, S and N, or R$^1$ is a substituted C$_{1-20}$-aliphatic group where at least one of the substituents is a paramagnetic chelate;

R$^2$ is a hydrogen or a substituted or unsubstituted C$_{1-6}$-aliphatic group, C$_{6-10}$-aryl group or C$_{7-20}$-araliphatic group;

R$^3$ is the residue of asteroid containing at least one alcohol or phenol group and which may be further substituted; the molecule of formula I containing at least one iodine or heavy metal atom and being metabolisable to products which are soluble in body fluids and are physiologically acceptable.

The metabolic products of the compounds according to the invention will be R$^1$COOH, R$^2$CHO, R$^3$OH and carbon dioxide.

Aliphatic groups may be straight or branched, saturated or unsaturated and comprise, for example, alkyl, alkenyl and alkynyl groups, e.g. methyl, ethyl, isopropyl, butyl or allyl groups. Araliphatic groups comprise monocarbocyclic aryl alkyl groups, for example benzyl groups. Aryl groups comprise mono- or bi-cyclic aryl groups, for example phenyl, tolyl or naphthyl groups. Heterocyclic groups comprise heterocyclic 5- or 6-membered rings which preferably have one hetero atom, for example furyl, thienyl or pyridyl groups.

Possible substituents in the above mentioned hydrocarbon groups R$^1$ and R$^2$ comprise hydroxyl, alkoxy, etherified thiol, N—C$_{1-6}$-alkylamino, N—C$_{1-6}$-acylamino, N—C$_{1-6}$-acyl-N—C$_{1-6}$ alkylamino-, carbamoyl- and N-C$_{1-6}$-alkylcarbamoyl groups as well as halogen and heavy metal, for example tungsten, atoms. It should be noted that aromatic rings, such as phenyl, may carry C$_{1-6}$-alkyl groups, as in tolyl groups. Substitutions may occur in combination, and in the same manner N-acyl- and N-alkyl groups can carry hydroxy or alkoxy or esterified hydroxyl groups.

Esterified hydroxyl groups may comprise C$_{1-6}$ acyloxy groups such as acetoxy groups. Adjacent hydroxyl groups may be etherified with a single bridging group, such as an acetonide group.

Halogen atoms comprise fluorine, chlorine, bromine and iodine. More than one halogen atom may be present in any particular group, as in the trifluoromethyl group. It is particularly preferred that the molecule as a whole carries several iodine atoms, for example at least three.

The group of heavy metal atoms includes all the transition and lanthanide metal atoms and other metal atoms such as Sr, Ga, In, Tl, Sn and Ba. For use as an X-ray contrast agent the following metal atoms are preferred: Ce, Y, Zr, Sr, Tc, Ru, Hf, In, W, Mo, Re, Os, Ba, Ga, Sn and Tl; however Mo and W are particularly preferred. For use as paramagnetic metal species the following metal atoms are preferred: Mn, Fe, Dy, Eu, Tb, Tm, Yb, Er and Ho and most particularly Gd.

It is particularly preferred that R$^1$ contains an iodinated phenyl group, preferably a triiodophenyl group, or a paramagnetic chelate, preferably a chelate containing manganese (II), gadolinium (III) or dysprosium (III). An iodinated group may be selected from the very wide range of choices of such groups which are found in commercial carboxylic acid or non-ionic amide X-ray contrast agents. Such groups include 2, 4, 6-triiodophenyl groups having at the 3- and 5-positions groups selected from carbamoyl, N-alkylcarbamoyl or N-hydroxyalkylcarbamoyl, acylamino, N-alkyl-acylamino and acylaminomethyl groups. In such groupings, acyl groups will commonly be acetyl groups and N-alkylacylamino groups will commonly be N-methylacetylamino groups. N-hydroxyalkylcarbamoyl groups will commonly comprise 1,3 or 2,3-dihydroxypropyl groups as the hydroxyalkyl moiety.

In the group R$^1$ the triiodophenyl group will preferably be linked directly to the carbonyl group, i.e. the compound of formula (I) will be an ester of a triiodobenzoic acid derivative, for example an X-ray contrast acid such as metrizoic acid, diatrizoic acid, iothalamic acid and ioxaglic acid.

It is also particularly preferred that R$^1$ contains a paramagnetic chelate in which the chelating group has more than four coordinate sites to the paramagnetic element. The paramagnetic chelate may be selected from the very wide range of such chelates found in the literature. A particularly interesting class of chelating substances for this purpose consists of aminopolycarboxy acids and derivatives of these, for example substances described by Bersworth in U.S. Pat. No. 2,407,645, Schering in EP 71564, EP 263059, EP 130934 and U.S. Pat. No. 4,647,447, Nycomed in EP 165728, EP 299795 and U.S. Pat. No. 4,826,673, Sherry in U.S. Pat. No. 4,639,365, Bracco in EP 230893 and EP 325762, Lauffer in WO 86/06605, Salutar in U.S. Pat. No. 4,746,507, EP 290047 and U.S. Pat. No. 4,687,659, and in quoted documents in these patent publications. Particularly preferred are chelates including DTPA, ethylene diamine tetraacetic acid (EDTA), triethylene tetraamine hexaacetic acid (TTHA), 1,4,7,10-tetraazacyclododecane-1,4,7,10-tetraacetic acid (DOTA), 10-(2-hydroxypropyl)-1,4,7,10-tetraazacyclododecane-1,4,7-triacetic acid (DO3A) and derivatives of these.

It is preferred that R$^2$ is hydrogen or a lower alkyl group, in particular hydrogen or methyl is preferred.

The contrast medium of the present invention is soluble or nearly insoluble in water, dependent on the choice of substituents in formula (I). Water soluble products will mainly be salts, for example bile acid conjugates.

The R$^3$-group is asteroid residue containing at least one alcohol or phenol group. Other possible substituents of the steroid skeleton include lower saturated and unsaturated, substituted or unsubstituted alkyl groups (C$_1$–C$_{10}$), hydroxyl, alkoxy, esterified hydroxyl and keto groups, carboxy acids, carboxy acid esters and halogens. Halogen atoms include fluorine, chlorine, bromine and iodine. More than one halogen atom may be present in any particular group, as in the trifluoromethyl group. Particularly preferred sterols of the present invention include cholesterol, bile acid, dehydrobile acid, metheolon, nandrolon, fluoxymesterone, testosterone, ethinyl estradiol, estriol, medroxyprogesterone, oxyprogesterone, desogestrel, levonorgestrel, norgestrel, noretisteron, ethynoidiol, lynestrenol, cyproteron, danazol, fluodrocortisone, hydrocortisone, cortisone, betamethasone, dexamethasone, methylprednisolone, prednisolone, triamcinolone, beclomethasone, budesonide, deoxymethasone, desonide, fluomethasone, fluonisolide, fluocinoloacetonide, fluocinonide, flucortolone, flupredniden, halcinonide, chlobetasole and mometason. Of these sterols cholesterol, bile acid and dehydro bile acid are particularly preferred.

Sterols containing a double bond in the ring structure and/or having $C_{1-8}$ alkyl, alkynyl, hydroxyl, keto and/or fluoride groups as substituents are preferred in the present invention.

However, after metabolic enzymolysis it is important that the metabolic products have sufficient water solubility at physiological pH to be excreted from the target organs. They should themselves be physiologically acceptable.

We have found that particulate compounds according to the present invention on intravenous administration appear to be captured by the reticuloendothelial system of the liver and spleen, the resulting accumulation of particles greatly assisting the imaging of these organs. On the other hand, the phagocytosing cells of the liver (Kupffer cells) contain lysosomes which possess a broad spectrum of hydrolyric enzymes including a number of esterases. Thus, once the particles are phagocytosed, they enter the lysosomes and are converted into water-soluble products which are subsequently excreted. The relative rapidity of the conversion of the compounds into water-soluble products significantly decreases the risk of toxic reactions.

As compared with liposomes, the particles of solid contrast media according to the invention have a very much higher contrast agent content. Thus, to achieve a desired level of contrast, as provided by a particular amount of iodine or heavy metal atom, a far smaller amount of material has to be used and the risk of producing lung emboli is greatly reduced. Furthermore, the particulate material according to the invention, which is commonly crystalline, is generally much more stable to storage than the previously proposed liposomes.

The water soluble compounds according to the invention are rapidly accumulated in the different organ systems (mainly the liver, gall bladder and suprarenal glands), and rapidly degrade to physiologically acceptable substances.

A further aspect of the present invention is aimed at contrast media containing water soluble compounds of formula I for oral or intravascular administration.

For oral administration the contrast medium may be in the form of a capsule, tablet or as a liquid solution.

The invention also provides injectable contrast media comprising a compound of formula I in suspension in a liquid for injection.

The compounds according to the invention, as a result of their contrast medium content, give enhanced imaging with X-ray and magnetic resonance imaging.

The compounds according to the invention rapidly accumulate in the target organs and are then retained in the organs, allowing imaging to take place on a more convenient timescale than with known non-ionic contrast agents where any retention in the target organ is transient.

Thus when maximum contrast agent concentration in the target organ (for example the liver) is reached, a concentration "plateau" is achieved which allows imaging to be carried out over a longer period. When the elimination of the contrast agent from the organ begins, it proceeds very quickly so that the contrast agent is eliminated from the body after a short period.

This profile of uptake and excretion for the target organs is particularly beneficial and represents a significant advantage over the prior art. The compounds of the invention also have low toxicity.

The mean particle size of the contrast agent, provided this is insoluble in water, will generally be within the range 0.002 to 7 micron, preferably 0.01 to 3 microns.

If the contrast agent contains one or more ionisable groups, the injectable product may be a sterile physiologically acceptable liquid containing a physiologically acceptable salt of the contrast agent. Physiologically acceptable salts include, among others, sodium, potassium, calcium and magnesium salts as well as organic salts of the quaternary ammonium type for example methyl glucamine.

The injectable liquid may be any sterile physiologically acceptable liquid such as physiological saline which may usefully contain a physiologically acceptable stabilising agent such as bovine serum albumin, human serum albumin, propylene glycol, gelatin, polyvinylpyrrolindone (for example having a molecular weight about 30 000 daltons) or a polysorbate (for example polysorbate 80), or combinations of two or more of these stabilising agents.

The contrast medium may be used in the enhancement of X-ray and magnetic resonance images of different tissue types, organs or organ types, preferably liver/gall bladder, suprarenal glands and spleen in humans or animals, and according to this method will then be administered orally or intravascuarly, generally intravenously, prior to imaging.

According to another aspect of the invention, the invention provides a method for generating an image of the human or non-human body, preferably the human body, which comprises oral or intravascular administration to the above mentioned body of a contrast media containing the compound of formula I and generation of an X-ray or magnetic resonance image, of at least a part of the above mentioned body.

The compounds according to the invention may be prepared in any convenient way. A further aspect of the invention is aimed at the preparation of the compounds of formula I by esterification of an acid of formula $R^1COOH$ or a functional derivative thereof, with a compound of formula X—$CHR^2.O.CO.OR^3$ where X is a leaving group such as a halogen atom or a mesyloxy or tosyloxy group. Where X represents a leaving group, the functional derivative of the acid of formula $R^1COOH$ will normally be salt such as a potassium salt. Such a reaction will normally be carried out in solution, for example in a polar solvent such as dimethylformamide.

The compound of X—$CHR^2.O.CO.OR^3$ where X is halogen may in turn be prepared from $R^2CHO$ and a compound of formula $X^1.CO.OR^3$, wherein $X^1$ is a halogen atom, in the presence of a base such as pyridine.

The intermediates X—$CHR^2.O.CO.OR^3$ where X is halogen, may in turn be prepared from $R^2CHO$ and a compound of formula X—$CHR^2.O.CO.Hal$ with an alcohol of formula $R^3OH$, Hal being a halogen atom. Where the group $R^3$ contains multiple hydroxyl groups, carboxy acids or other reactive groups, it may be desirable to protect certain of these with, for example, acetonide groupings, in order to ensure reaction at a single functional group. Such acetonide groups may if desired remain in the final compound according to the invention.

Another aspect of the invention is aimed at a method of preparation of a contrast medium containing the compound of formula I dissolved in the soluble carrier or dispersed in water. The particulate form of the contrast agent according to the invention may advantageously be prepared by precipitation from solution in a water-miscible solvent such as ethanol by admixture with water, which may conveniently contain a stabilising agent such as bovine serum albumin, human serum albumin, gelatin, polyvinylpyrrolidone, propylene, glycol or a polysorbate, with vigorous agitation, e.g. using ultrasound. In this way, it is possible to obtain particles of mean diameter in the order 1.0 microns. Mechanical crushing or spray drying, for example to an appropriate particle size is also suitable. The particles may be dispersed in the liquid for injection referred to above.

The following examples are given by way of illustration only.

EXAMPLE 1

Amidotrizoinic acid (diatrizoic acid) cholesterol conjugate 1 mmol cholesterol is reacted with 1.1 mmol 1-chloroethyl chloroformate in 25 ml dichloromethane in presence of pyridine (0.5 ml). The chloroacetate derivative of cholesterol is allowed to react further with the sodium salt of amidotrizoinic acid in DMF (30 ml) at 70° C. for 8 hours. The mixture is evaporated in a rotavapor and the amidotrizoinic acid conjugated with cholesterol is isolated by chromatography (silica, chloroform).

EXAMPLE 2

GdDOTA bile acid conjugate 1 mmol bile acid benzyl ester is reacted with 1.1 mmol 1-chloroethyl chloroformate in 50 ml dichloromethane in the presence of pyridine (2 ml). The 3-chloroacetate derivative of bile acid benzyl ester is allowed to react with an excess of the sodium salt of DOTA (5 mmol) in DMF (30 ml) at 80° C. for 12 hours. The mixture is evaporated on a rotavapor and the DOTA conjugated with bile acid benzyl ester is isolated by ion exchange chromatography. The product undergoes a further catalytic hydrogenation (Pd on C) to remove the benzyl group. The gadolinium complex is prepared by allowing bile acid-DOTA conjugate to react with stoichiometric amounts of gadolinium acetate. The acetic acid formed is removed by repeated rotary evaporations with water.

EXAMPLE 3

Particle preparation

Bovine serum albumin, BSA (0.75 g) was dissolved in distilled water (25.0 ml) and filtered through a membrane filter with pore size 0.45 micron. A filtered solution (0.22 micron) of the product of Example 1 (0.2 g) in 96% ethanol (0.5 ml) was slowly added to the BSA solution under vigorous stirring over a prolonged period of time. The resulting microparticles were centrifuged and washed repeatedly. The size and size distribution of the particles were analyzed using a Coulter Multisizer and by light- and electron-microscopy.

EXAMPLE 4

Pharmaceutical formulation

The particles of Example 3 (1.0 g) were suspended in a sterile filtered 0.9% sodium chloride/water for injection solution (100 ml) under vigorous stirring until a homogenous suspension was achieved.

EXAMPLE 5

Synthesis of 3-(1-chloroethoxycarbonyl) cholesterol

The product was prepared as described in Dang, V. A., Olofson, R. A., J. Org. Chem. 55 (1990) 1847–1851.

Pyridine (0.27g, 3.4 mmol) was dripped into a stirred, cooled (0° C.) solution of 1-chloroethyl chloroformate (0.44 g, 3.1 mmol) and cholesterol (1.12 g, 2.9 mmol) in $CH_2Cl_2$ (2 ml). After 3 hours at room temperature the mixture was diluted with $CH_2Cl_2$ (30 ml) and washed with 0.5M HCl (25 ml) and water (3×25 ml), dried over $NaSO_4$ and evaporated to dryness.

| Yield: | 1.43 g (99.3%) | |
|---|---|---|
| mp: | 65–68° C. | |
| TLC: | $R_f$ = 0.64 (1% MeOH/CHCl$_3$) | |
| CH: | | |

| | % C | % H |
|---|---|---|
| Calculated: | 73.06 | 10.02 |
| Found: | 73.34 | 10.03 |

Synthesis of 3-[1-(3,5-Diacetamido-2,4,6-triiodobenzoyloxy)-ethoxycarbonyl]-cholesterol Method A Diatrizoic acid cesium salt (2.04 g, 3.0 mmol) was added to a stirred mixture of 3-(1-chloroethoxycarbonyl)-cholesterol (1.64 g, 3.3 mmol), NaI (0.045 g, 0.3 mmol) and 18-Crown-6 (0.079 g, 0.3 mmol) in DMF (50 ml). The mixture was kept at 80° C. for 4 days. The mixture was cooled, diluted with CHCl$_3$ (150 ml) and washed with saturated aqueous NaHCO$_3$ (3×150 ml), water (2×150 ml). The organic phase was dried with Na$_2$SO$_4$ and evaporated. The product was purified by flash chromatography on silica (5% MeOH/CHCl$_3$).

Method B

Diatrizoic acid tetrabutyl ammonium salt (1.73 g, 2.0 mmol) was added to a stirred mixture of 3-(1-chloroethoxycarbonyl)-cholesterol (1.00 g, 2.0 mmol) and KI (0.04 g, 0.24 mmol) in DMF (30 ml). After 3 hours at 60° C. the mixture was cooled and diluted with CHCl$_3$. The organic phase was washed with saturated aqueous NaHCO$_3$ (4×150 ml), water (2×150 ml) and dried over Na$_2$SO$_4$. The product was purified by flash chromatography on silica (5% MeOH/CHCl$_3$).

| Yield Method | Yield g | % |
|---|---|---|
| A | 0.87 | 29.7 |
| B | 1.41 | 65.89 |

| mp: | 221–222° C. (decomp) | | |
|---|---|---|---|
| TLC: | $R_f$ = 0.20 (1% MeOH/CHCl$_3$) | | |
| | $R_f$ = 0.38 (5% MeOH/CHCl$_3$) | | |
| CH: | | | |

| | % C | % H | % N |
|---|---|---|---|
| Calculated: | 45.99 | 5.37 | 2.61 |
| Found: | 45.75 | 5.27 | 2.87 |

EXAMPLE 6

Synthesis of Methyl 3-(1-Chloroethoxycarbonyl)-cholate 1-chloroethyl chloroformate (1.85 g, 12.9 mmol) was added dropwise to a stirred cooled (0° C.) solution of methyl cholate (4.2 g, 10 mmol) in pyridine (20 ml). After 1 hour at room temperature the mixture was diluted with CHCl$_3$ (200 ml). The organic phase was washed with 0.5M HCl (2×100 ml), water (100 ml), dried over Na$_2$SO$_4$ and evaporated to dryness. Purified by flash chromatography on silica (25% EtAc/Hexane).

| Yield: | 4.38 g (83.3%) |
|---|---|
| mp: | 90–96° C. |
| TLC: | R$_f$ = 0.83 (10% MeOH/CHCl$_3$) |
| CH: | |

| | % C | % H |
|---|---|---|
| Calculated: | 63.44 | 8.75 |
| Found: | 63.45 | 8.67 |

| $^1$HNMR: Multiplicity | CD$_2$Cl$_2$ ppm | Interpretation |
|---|---|---|
| s | 0.72 | 18 CH$_3$ |
| s | 0.95 | 19 CH$_3$ |
| d | 0.98 | 21 CH$_3$ |
| d | 1.81 | CH$_3$—CHCl |
| s | 3.60 | OCH$_3$ |
| m | 3.83 | 12 H |
| m | 3.96 | 7 H |
| m | 4.46 | 3 H |
| q | 6.37 | CHCl—CH$_3$ |

| $^{13}$CNMR: | CD$_2$Cl$_2$ | | | | | | |
|---|---|---|---|---|---|---|---|
| C no | ppm | C no | ppm | C no | ppm | C no | ppm |
| 1 | 35.59 | 8 | 39.67 | 15 | 23.46 | 22 | 31.23 |
| 2 | 31.23 | 9 | 26.85 | 16 | 27.75 | 23 | 31.23 |
| 3 | 79.88 | 10 | 34.92 | 17 | 47.41 | 24 | 174.55 |
| 4 | 39.67 | 11 | 28.31 | 18 | 12.57 | 25 | 51.55 |
| 5 | 41.99 | 12 | 73.16 | 19 | 22.42 | 26 | 152.33 |
| 6 | 34.92 | 13 | 46.71 | 20 | 35.59 | 27 | 84.79 |
| 7 | 68.47 | 14 | 41.99 | 21 | 17.46 | 28 | 25.39 |

| MS |
|---|
| 551.5 = M + Na |
| 529.5 = M + H |
| 511.4 = M + H − H$_2$O |
| 493.6 = M + H − HCl |
| 495.5 = M − (18 + CH$_3$(15)) |
| 479.5 = M − (18 + OCH$_3$) |

Synthesis of Benzyl 3-(1-Chloroethoxycarbonyl)-cholate 1-chloroethyl chloroformate (1.29 g, 9.0 mmol) was added dropwise to a stirred cooled (0° C.) solution of benzylcholate (3.00 g, 6.0 mmol) in pyridine (20 ml). After 1 hour at room temperature the mixture was diluted with CHCl$_3$ (200 ml). The organic phase was washed with 0.5M HCl (2×100 ml), water (100 ml), dried over Na$_2$SO$_4$ and evaporated to dryness. Purified by flash chromatography on silica (25% EtAc/Hexane).

| Yield: | 2.35 g (69.9%) |
|---|---|
| mp: | 61–67° C. |
| TLC: | R$_f$ = 0.85 (25% MeOH/CHCl$_3$) |
| CH: | |

| | % C | % H |
|---|---|---|
| Calculated: | 67.48 | 8.16 |
| Found: | 67.24 | 8.26 |

| $^1$HNMR: Multiplicity | CD$_2$Cl$_2$ ppm | Interpretation |
|---|---|---|
| s | 0.68 | 18 CH$_3$ |
| s | 0.92 | 19 CH$_3$ |
| d | 0.97 | 21 CH$_3$ |
| d | 1.79 | CH$_3$—CHCl |
| m | 3.84 | 12 H |
| m | 3.98 | 7 H |
| m | 4.49 | 3 H |
| s | 5.09 | CH$_2$—C$_6$H$_5$ |
| q | 6.41 | CHCl—CH$_3$ |
| m | 7.34–7.37 | C$_6$H$_5$ |

| $^{13}$CNMR: | CD$_2$Cl$_2$ | | | | | | |
|---|---|---|---|---|---|---|---|
| C no | ppm | C no | ppm | C no | ppm | C no | ppm |
| 1 | | 10 | 34.94 | 19 | 22.53 | 28 | 128.6 |
| 2 | 30.05 | 11 | 28.69 | 20 | 53.49 | 29 | 128.6 |
| 3 | 79.97 | 12 | 73.14 | 21 | 17.45 | 30 | 128.6 |
| 4 | 39.88 | 13 | 46.81 | 22 | 31.24 | 31 | 128.6 |
| 5 | 42.24 | 14 | 42.24 | 23 | 31.58 | 32 | 152.62 |
| 6 | 35.27 | 15 | 26.80 | 24 | 174.15 | 33 | 84.99 |
| 7 | 68.50 | 16 | 27.74 | 25 | 66.27 | 34 | 25.43 |
| 8 | 39.88 | 17 | 47.54 | 26 | 167.8 | | |
| 9 | 26.94 | 18 | 12.61 | 27 | 128.6 | | |

| MS |
|---|
| 627.5 = M + Na |
| 605.5 = M + H |
| 587.4 = M + H − H$_2$O |
| 569.5 = M + H − HCl |
| 479.4 = M − 18 − OCH$_2$C$_6$H$_5$ |

Synthesis of t-Butyl 3-(1-Chloroethoxycarbonyl)-cholate

Method A 1-chloroethyl chloroformate (0.40 g, 2.8 mmol) was added dropwise to a stirred cooled (0° C.) solution of t-butylcholate (1.00 g, 2.2 mmol) and dimethylaminopyridine (0.36 g, 2.9 mmol) in CH$_2$Cl$_2$ (15 ml). After 24 hours at room temperature and refluxing for 20 minutes the solution was cooled and diluted with CH$_2$Cl$_2$ (100 ml) and washed with saturated aqueous CuSO4 (x4), saturated aqueous NaHCO$_3$ (x2) and brine (x1). The organic phase was dried over MgSO$_4$ and evaporated. Purified by column chromatography on alumina grade 1 (0.5% MeOH/CHCl$_3$).

Method B 1-chloroethyl chloroformate (0.6 g, 4.2 mmol) was added dropwise to a stirred cooled (0° C.) solution of t-butylcholate (1.50 g, 3.2 mmol) in pyridine (15 ml). After 1 hour at 50° C. the mixture was cooled and diluted with CHCl$_3$ (100 ml). The organic phase was washed with water (4×100 ml), water (100 ml) followed by 1M H$_2$SO$_4$ (100 ml). The organic phase was then washed with saturated aqueous NaHCO$_3$ (100 ml), water (100 ml) and dried over Na$_2$SO$_4$ and evaporated. Purified by column chromatography on alumina grade 1 (0.5% MeOH/CHCl$_3$).

| Yield Method | gram | % |
|---|---|---|
| A | 1.04 | 84.6 |
| B | 1.54 | 83.7 |

| mp: | 76–80° C. |
|---|---|
| TLC: | R$_f$ = 0.66 (5% MeOH/CHCl$_3$) |
| CH: | |

| | % C | % H |
|---|---|---|
| Calculated: | 65.19 | 9.00 |
| Found: | 65.24 | 9.34 |

-continued

| ¹HNMR: Multiplicity | CD₂Cl₂ ppm | Interpretation |
|---|---|---|
| s | 0.67 | 18 CH₃ |
| s | 0.92 | 19 CH₃ |
| d | 0.96 | 21 CH₃ |
| s | 1.42 | C(CH₃)₃ |
| d | 1.79 | CH₃—CHCl |
| m | 3.84 | 7 H |
| m | 3.98 | 12 H |
| m | 4.47 | 3 H |
| q | 6.52 | CHCl—CH₃ |

| ¹³CNMR: | | CD₂Cl₂ | | | | | |
|---|---|---|---|---|---|---|---|
| C no | ppm | C no | ppm | C no | ppm | C no | ppm |
| 1 | 35.55 | 9 | 26.85 | 17 | 47.59 | 25 | 79.95 |
| 2 | 31.34 | 10 | 34.96 | 18 | 12.60 | 26 | 28.21 |
| 3 | 84.90 | 11 | 28.51 | 19 | 22.48 | 27 | 28.21 |
| 4 | 39.78 | 12 | 73.25 | 20 | 35.55 | 28 | 28.21 |
| 5 | 41.59 | 13 | 46.81 | 21 | 17.53 | 29 | 154.43 |
| 6 | 34.97 | 14 | 42.17 | 22 | 32.83 | 30 | 79.95 |
| 7 | 68.52 | 15 | 23.50 | 23 | 31.34 | 31 | 25.47 |
| 8 | 39.78 | 16 | 28.21 | 24 | 173.60 | | |

MS (EI)

480 = M − 18 − OC(CH₃)₃
395 = M − side chain − 18
354 = M − 57 − CHCl(CH₃)OCO
389.5 = M − 57 − CHCl(CH₃)OCO − O A) Synthesis of Methyl 3-[1-(3,5-Diacetamido-2,4,6-triiodobenzoyloxy)-ethycarbonyl]-cholate Diatrizoic acid tetrabutylammonium salt (0.94 g, 1.1 mmol) was added to a solution of methyl 3-(1-chloroethoxycarbonyl)-cholate (0.54 g, 10 mmol) and KI (0.02 g, 0.12 mmol) in DMF (25 ml). After 4 hours at 60° C. the solution was cooled and diluted with 150 ml CHCl₃ and washed with saturated aqueous NaHCO₃ (5×100 ml) followed by water (2×100 ml). The organic phase was dried over Na₂SO₄ and evaporated. Purified by flash chromatography on silica (5% MeOH/CHCl₃).

| Yield: | 0.84 g (75.7%) |
| mp: | 180–186° C. (decomp) |
| TLC: | R_f = 0.83 (25% MeOH/CHCl₃) |
| CH: | |

| | % C | % H | % N |
|---|---|---|---|
| Calculated: | 42.31 | 4.88 | 2.53 |
| Found: | 42.15 | 4.81 | 2.59 |

| ¹HNMR: Multiplicity | CD₂Cl₂ ppm | Interpretation |
|---|---|---|
| s | 0.66 | 18 CH₃ |
| m | 0.90 | 19 CH₃ |
| m | 1.07 | 21 CH₃ |
| s | 1.74 | CH₃—CHO₂ |
| s | 2.18 | CH₃CONH |
| s | 3.63 | OCH₃ |
| m | 3.81 | 7 H |
| m | 3.94 | 12 H |
| m | 4.45 | 3 H |
| m | 7.05 | CH(OCO)₂ |
| d | 8.9 | NH |

| ¹³CNMR: | | CD₂Cl₂ | | | | | |
|---|---|---|---|---|---|---|---|
| C no | ppm | C no | ppm | C no | ppm | C no | ppm |
| 1 | 35.65 | 11 | 28.56 | 21 | 17.48 | 31 | 95.58 |
| 2 | 31.25 | 12 | 73.00 | 22 | 31.25 | 32 | 144.6 |
| 3 | 80.04 | 13 | 46.73 | 23 | 31.46 | 33 | 108 |
| 4 | 39.79 | 14 | 41.53 | 24 | 175.0 | 34 | 144.6 |
| 5 | 41.53 | 15 | 23.52 | 25 | 51.72 | 35 | 95.98 |
| 6 | 34.96 | 16 | 27.81 | 26 | 152.6 | 36 | 169.95 |
| 7 | 68.30 | 17 | 47.52 | 27 | 93.56 | 37 | 23.8 |
| 8 | 39.79 | 18 | 12.60 | 28 | 26.89 | 38 | 169.95 |
| 9 | 26.89 | 19 | 22.49 | 29 | 166.5 | 39 | 23.8 |
| 10 | 34.96 | 20 | 35.65 | 30 | 146.6 | | |

MS 1129.2 = M + Na
1003.5 = M + Na + H − I
1107.5 = M + H
981.5 = M + 2H − I
855 = M + 3H − 2I
729.6 = M + 4H − 3I

B) Synthesis of Benzyl 3-[1-(3,5-Diacetamido-2,4,6-triiodobenzoyloxy)-ethoxycarbonyl]-cholate Diatrizoic acid tetrabutylammonium salt (1.35 g, 1.6 mmol) was added to a solution of benzyl 3-(1-chloroethoxycarbonyl)-cholate (0.87 g, 1.4 mmol) and KI (0.03 g, 0.18 mmol) in DMF (20 ml). After 4 hours at 60° C. the solution was cooled and diluted with 100 ml CHCl₃ and washed with saturated aqueous NaHCO₃ (5×100 ml) followed by water (2×100 ml). The organic phase was dried over Na₂SO₄ and evaporated. Purified by flash chromatography on silica (5% MeOH/CHCl₃).

| Yield: | 1.29 g (75.9%) |
| mp: | 196–200° C. (decomp) |
| TLC: | R_f = 0.53 (10% MeOH/CHCl₃) |
| CH: | |

| | % C | % H | % N |
|---|---|---|---|
| Calculated: | 45.7 | 4.86 | 2.37 |
| Found: | 45.61 | 5.08 | 2.32 |

| ¹HNMR: Multiplicity | CD₂Cl₂ ppm | Interpretation |
|---|---|---|
| s | 0.65 | 18 CH₃ |
| s | 0.90 | 19 CH₃ |
| d | 1.07 | 21 CH₃ |
| d | 1.36 | CH₃CH(OCO)₂ |
| s | 2.00 | CH₃CONH |
| m | 3.77 | 7 H |
| m | 3.95 | 12 H |
| m | 4.45 | 3 H |
| s | 5.02 | CH₂—Ar |
| q | 7.05 | CHCH₃(OCO)₂ |
| m | 7.35 | Ar—H |
| m | 8.85 | NH |

| ¹³CNMR: | | CD₂Cl₂ | | | |
|---|---|---|---|---|---|
| C no | ppm | C no | ppm | C no | ppm |
| 1 | 35.60 | 12 | 73.00 | 23 | 31.49 |
| 2 | 31.24 | 13 | 46.79 | 24 | 174.32 |
| 3 | 80.00 | 14 | 42.15 | 25 | 66.29 |
| 4 | 40.00 | 15 | 23.77 | 26 | |
| 5 | 42.15 | 16 | 28.50 | 27 | |
| 6 | 34.94 | 17 | 47.50 | 28 | 152.5 |
| 7 | 68.40 | 18 | 12.58 | 29 | 96.00 |

| | | | | | |
|---|---|---|---|---|---|
| 8 | 40.00 | 19 | 22.47 | 30 | 26.87 |
| 9 | 27.07 | 20 | 35.60 | 31 | 166.5 |
| 10 | 35.21 | 21 | 17.46 | 32 | 146.0 |
| 11 | 28.50 | 22 | 31.73 | 33 | 93.59 |

C) Synthesis of t-Butyl 3-[1-(3,5-diacetamido-2,4,6-triiodobenzoyloxy)-ethoxycarbonyl]-cholate Diatrizoic acid tetrabutylammonium salt (0.99 g, 1.2 mmol) was added to a solution of t-butyl 3-(1-chloroethoxycarbonyl)-cholate (0.87 g, 1.4 mmol) and KI (0.02 g, 0.12 mmol) in DMF (20 ml). After 3 hours at 60° C. the solution was cooled and diluted with 100 ml $CHCl_3$ and washed with saturated aqueous $NaHCO_3$ (4×100 ml) followed by water (2×100 ml). The organic phase was dried over $Na_2SO_4$ and evaporated. Purified by column chromatography on alumina grade 1 (3% MeOH/$CHCl_3$).

| Yield: | 0.88 g (79.3%) |
|---|---|
| mp: | 196–201° C. (decomp) |
| TLC: | $R_f$ = 0.15 ($SiO_2$ 5% MeOH/$CHCl_3$) |
| CH: | |

| | % C | % H | % N |
|---|---|---|---|
| Calculated: | 43.92 | 4.18 | 2.44 |
| Found: | 43.75 | 5.22 | 2.55 |

| $^1$HNMR: Multiplicity | $CD_2Cl_2$ ppm | Interpretation |
|---|---|---|
| s | 0.67 | 18 $CH_3$ |
| m | 0.89 | 19 $CH_3$ |
| m | 1.13 | 21 $CH_3$ |
| s | 1.42 | $C(CH_3)_3$ |
| s | 2.17 | $CH_3CH(OCO)_2$ |
| m | 3.81 | 7 H |
| m | 3.95 | 12 H |
| m | 4.43 | 3 H |
| m | 7.34 | $CH(OCO)_2CH_3$ |
| m | 8.85 | NH |

D) Synthesis of 3-[1-(3,5-Diacetamido-2,4,6-triiodobenzoyloxy)ethoxycarbonyl]-cholic Acid Trifluoroacetic acid (1.5 ml) was added to a stirred, cooled solution (0° C.) of t-butyl-3-[1-(3,5-diacetamido-2,4,6-triiodobenzoyloxy)-ethoxycarbonyl]-cholate (0.20 g, 0.18 mmol) in $CH_2Cl_2$ (5 ml). After 45 minutes at room temperature, the solution was diluted with ethyl acetate (50 ml) and washed with water (3×50 ml). The organic phase was dried over $Na_2SO_4$ and purified by flash chromatography on silica (20% MeOH/$CHCl_3$).

| Yield: | 0.18 g (94.7%) | | |
|---|---|---|---|
| mp: | 217–220° C. (decomp) | | |
| TLC: | $R_f$ = 0.42 (20% MeOH/$CHCl_3$) | | |
| $^1$HNMR: | DMSO $D_6$ | | |
| 0.606 ppm | s | 18 $CH_3$ | |
| 0.858 ppm | s | 19 $CH_3$ | |
| 0.935 ppm | d | 21 $CH_3$ | |
| 1.693 ppm | d | $CH_3CH(OH)_2$ | |
| 2.18 ppm | s | $CH_3CONH$ | |
| 3.807 ppm | m | 12 H | |
| 4.231 ppm | m | 7 H | |
| 4.443 ppm | m | 3 H | |
| 9.94 ppm | q | $CH(O)_2CH_3$ | |
| 10.132 | d | NH | |

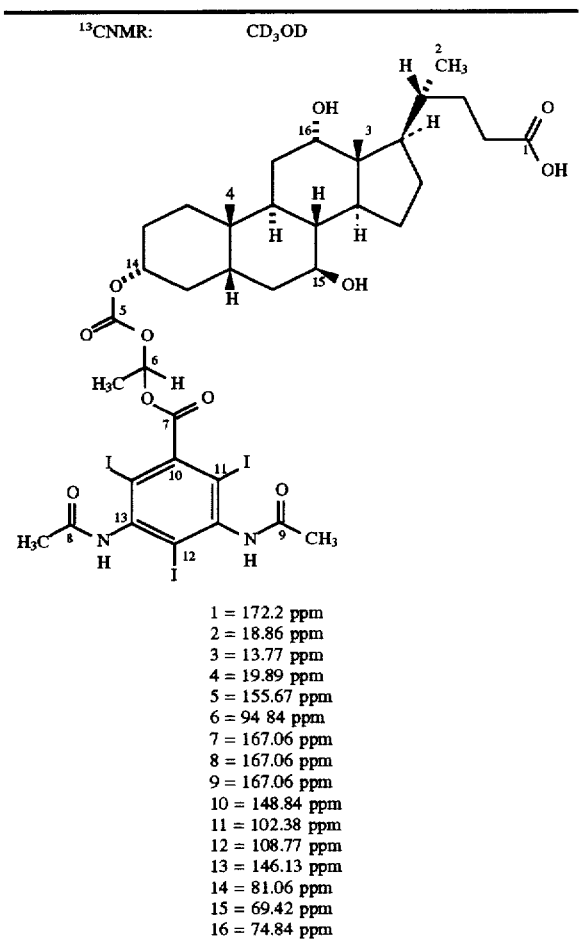

| $^{13}$CNMR: | $CD_3OD$ |
|---|---|
| 1 = 172.2 ppm | |
| 2 = 18.86 ppm | |
| 3 = 13.77 ppm | |
| 4 = 19.89 ppm | |
| 5 = 155.67 ppm | |
| 6 = 94.84 ppm | |
| 7 = 167.06 ppm | |
| 8 = 167.06 ppm | |
| 9 = 167.06 ppm | |
| 10 = 148.84 ppm | |
| 11 = 102.38 ppm | |
| 12 = 108.77 ppm | |
| 13 = 146.13 ppm | |
| 14 = 81.06 ppm | |
| 15 = 69.42 ppm | |
| 16 = 74.84 ppm | |

EXAMPLE 7

3-(Chloromethoxycarbonyl) Cholesterol

Chloromethyl chloroformate (1.96 g, 15.2 mmol) and cholesterol (5.0 g, 12.9 mmol) was dissolved in $CH_2Cl_2$ (10 ml). The solution was cooled. Pyridine (1.21 g, 15.3 mmol) was dripped into the stirred solution over 5 minutes. Heat was produced and the reaction gave a clear solution from a somewhat unclear starting solution. After 24 hours at room temperature, the mixture was diluted with $CH_2Cl_2$ (50 ml), washed with 0.5M HCl (50 ml) and water (3×25 ml). After treatment with $MgSO_4$, the solution was evaporated to dryness.

| Yield: | 6.02 g (97.4%) |
|---|---|
| mp: | 87–89° C. |
| TLC: | $R_f$ = 0.87 (EtAc/Hexane 1:5) |
| Mw: | 479.1 |
| $^1$H-NMR ($CDCl_3$): delta = | 4.55 (O$CH$($CH_2$)$_2$; 5.38 (C=$CHCH_2$); 5.71 (O$CH_2$Cl); |
| $^{13}$C-NMR ($CDCl_3$): delta = | 12.60; 19.38; 19.91; 21.68; 28.20; 23.45; 24.45; 24.87; 28.08; 28.56; 28.78; 32.31; 32.39; 36.26; 36.64; 36.94; 37.21; 38.23; 39.93; 40.10; 40.68; 50.23; 56.34; 56.86; 72.06; 79.28; 122.72; 138.19; 151.70. |

| | |
|---|---|
| MS: | 147, 247, 359, 368, 389, 404, 363, 478, 481. |
| Elemental analysis gave: | 72.87% C, 9.79% H |
| Calculated: | 72.70% C, 9.89% H |

3-[1-(3,5-Diacetamido-2,4,6-triiodobenzoyloxy)-methoxycarbonyl]-cholesterol 3-(Chloromethoxycarbonyl)cholesterol (3.0 g, 6.26 mmol) in dry DMF (200 ml) was added dropwise at 50° C. to a stirred solution of potassium 3,5-diacetamido-2,4,6-triiodobenzenecarboxylate (3.9 g, 6.0 mmol) and NaI (0.37 g, 2.5 mmol) in dry DMF (200 ml). A precipitate was formed. After stirring for 17 hours, the precipitate was removed by filtration and the solvent removed at reduced pressure. The residue was triturated and washed repeatedly in water and recrystallised from chloroform/methanol.

| | |
|---|---|
| Yield: | 5.3 g (84%) |
| mp: | 263.6° C. (decomp.) |
| TLC: | $R_f = 0.59$ (EtAc) |
| Mw: | 1051 |
| $^1$H-NMR (DMSO-d6): delta = | 2.02 (NCOC$\underline{H}_3$); 5.92 (OC$\underline{H}_2$O); 10.10 (NH). |
| $^{13}$C-NMR (DMSO-d6): delta = | 11.99; 18.79; 19.16; 22.60; 22.86; 23.16; 23.56; 27.60; 31.46; 35.37; 35.80; 36.09; 38.28; 49.32; 55.49; 55.97; 77.86; 82.01; 96.19; 108.79; 121.52; 137.84; 143.41; 144.10; 151.26; 164.88; 166.08; 166.31. |
| Elemental analysis: | 45.71% C, 5.17% H |
| Calculated: | 45.47% C, 5.25% H |

We claim:

1. Metabolically labile esters of the formula I

(I)

wherein

R$^1$ is a substituted or unsubstituted C$_{1-20}$ aliphatic, araliphatic or C$_{6-20}$ aryl group or a C$_{1-20}$ heterocyclic group having one or more hetero atoms selected from O, S and N, said group containing at least one iodine or heavy metal atom; or R$^1$ is a substituted C$_{1-20}$-aliphatic group where at least one of the substituents is a paramagnetic metal containing chelate;

R$^2$ is a hydrogen or a substituted or unsubstituted C$_{1-6}$ aliphatic, C$_{6-10}$ aryl or C$_{7-20}$ araliphatic group;

R$^3$ is a steroidal group containing at least one alcohol or phenol group and which may be further substituted;

the compound of formula I being metabolisable to products which are soluble in body fluids and are physiologically acceptable.

2. Metabolically labile esters as claimed in claim 1 wherein R$^1$ comprises an iodinated phenyl group.

3. Metabolically labile esters as claimed in claim 1 wherein R$^1$ comprises a chelate of manganese (II), gadolinium (III) or dysprosium (III).

4. Metabolically labile esters as claimed in claim 1 wherein R$^3$ comprises a cholesterol, bile acid or dehydro bile acid residue.

5. A process for the preparation of a metabolically labile ester as claimed in claim 1 comprising esterification of an acid of formula R$^1$COOH or a functional derivative thereof, in which R$^1$ is as defined in claim 1, with a compound of formula X—CHR$^2$O.CO.OR$^3$ in which X is a leaving group and R$^2$ and R$^3$ are as defined in claim 1.

6. A contrast medium for X-ray or magnetic resonance imaging by injection which comprises a compound of formula I according to claim 1 dissolved or suspended in a physiologically acceptable liquid.

7. A contrast medium as claimed in claim 6 comprising a compound of formula I with a particle size in the range 0.01 to 3 microns.

8. A contrast medium for X-ray or magnetic resonance imaging by oral administration which comprises a compound of formula I according to claim 1 in tablet or capsule form, or as a liquid solution.

9. A method of generating an image of a human or non-human animal body comprising oral or intravascular administration of a contrast medium according to claim 6 and generation of an X-ray or magnetic resonance image of at least part of said body.

10. A method as claimed in claim 9 for generating an image of a human body.

* * * * *